(12) United States Patent
Xu et al.

(10) Patent No.: US 12,305,162 B2
(45) Date of Patent: May 20, 2025

(54) **METHOD FOR EXPANDING PROPAGATION OF *METARHIZIUM rILEYI* MR006 AND USE THEREOF**

(71) Applicant: Institute of Plant Protection and Agro-Products Safety, Anhui Academy of Agricultural Sciences, Hefei (CN)

(72) Inventors: Tingting Xu, Hefei (CN); Feilong Wu, Hefei (CN); Xiujun Wu, Hefei (CN); Fei Hu, Hefei (CN); Lina Xu, Hefei (CN); Sijia Bi, Hefei (CN); Youmin Tong, Hefei (CN); Benjin Hu, Hefei (CN); Xianyan Su, Hefei (CN); Yong Zhang, Hefei (CN)

(73) Assignee: Institute of Plant Protection and Agro-Products Safety, Anhui Academy of Agricultural Sciences, Hefei (CN)

( * ) Notice: Subject to any disclaimer, the term of this patent is extended or adjusted under 35 U.S.C. 154(b) by 0 days.

(21) Appl. No.: 18/734,239

(22) Filed: Jun. 5, 2024

(65) Prior Publication Data

US 2024/0409881 A1    Dec. 12, 2024

(30) Foreign Application Priority Data

Jun. 5, 2023    (CN) .......................... 202310657300.6

(51) Int. Cl.
   *C12N 1/14*    (2006.01)

(52) U.S. Cl.
   CPC ...................................... *C12N 1/14* (2013.01)

(58) Field of Classification Search
   CPC ....................................................... C12N 1/14
   See application file for complete search history.

(56) References Cited

FOREIGN PATENT DOCUMENTS

| CN | 111548944 A | 8/2020 |
|---|---|---|
| CN | 111662828 A | 9/2020 |
| CN | 112812976 A | 5/2021 |
| CN | 115747130 A | 5/2022 |
| JP | H05236948 A | 9/1993 |
| KR | 20150057124 A | 5/2015 |

*Primary Examiner* — Suzanne M Noakes
(74) *Attorney, Agent, or Firm* — Shen Huang

(57) ABSTRACT

The present invention relates to the field of microbial culture, in particular to a method for expanding propagation and producing spores of *Metarhizium rileyi* and use thereof. In the present invention, *Metarhizium rileyi* Mr006 is sprayed on 2nd instar live larvae of *Spodoptera litura* treated with a sub-lethal dose of chlorantraniliprole to cause infection, the 2nd instar larvae of the *Spodoptera litura* infected with the *Metarhizium rileyi* Mr006 spores are concentrated into a sterile box, placed into an artificial climate box and continuously fed with an artificial feed until death or pupation, the infection condition of the insect bodies is observed, spores are collected after a 1st complete spore production, after the infected insects are subjected to moisture preservation, expanded propagation and culture are continuously performed, and the spores are repeatedly collected twice to obtain the maximum spore yield.

7 Claims, No Drawings

METHOD FOR EXPANDING PROPAGATION OF *METARHIZIUM rILEYI* MR006 AND USE THEREOF

TECHNICAL FIELD

The present invention relates to the field of microbial culture, in particular to a method for expanding propagation and producing spores of *Metarhizium rileyi* and use thereof.

BACKGROUND

At present, the harm of pests on crops is one of the major factors causing agricultural yield reduction. The long-term large-scale use of chemical pesticides can kill pests, but brings a series of side effects of pesticide residue exceeding of agricultural products, year-by-year rising of the pest resistance level, environmental pollution and the like. In view of this, biological control is being increasingly emphasized, and pest control using entomopathogenic microorganisms is one of the important means for biological control of pests. Compared with other insecticidal microorganisms, the insecticidal fungi have the advantages of easy prevalence, environmental friendliness, difficulty in generation of drug resistance and the like, and therefore play an important role in biological control of pests.

*Metarhizium rileyi* is an entomopathogenic fungus widely distributed in China, frequently causes high-intensity insect epidemic diseases in the nature, can infect various lepidopteran pests, and particularly has extremely high infectivity on noctuid pests such as *Spodoptera frugiperda, Spodoptera litura, Helicoverpa armigera*, and *Spodoptera exigua*, thereby having higher development and utilization values. However, most research works require indoor artificial culture of fungi, and the nutrient composition requirements of different fungi on culture mediums are greatly different. The strain expanded propagation is an important factor influencing the application prospect. Currently, the *Metarhizium rileyi* fermentation mostly uses cheap agricultural and sideline products such as wheat bran, corn flour, rice flour and the like as nutrient substances so as to obtain the maximum spore yield, but the spore yield is still limited. The most commonly used Sabouraud maltose-yeast culture medium and potato culture medium for culturing the *Metarhizium rileyi* in a laboratory have the problems of low spore production rate, low spore germination rate, long spore production period, high cost, rapid strain degeneration and the like.

SUMMARY

*Metarhizium rileyi* Mr006 of the present invention is obtained by isolating and identifying *Spodoptera frugiperda* infected with entomogenous fungi in the fields discovered in the investigation of the Taihe corn planting area by the biological control team of the Institute of Plant Protection and Agro-Products Safety, Anhui Academy of Agricultural Sciences. The *Metarhizium rileyi* Mr006 has been published in Chinese patent application of No. CN202210572361.8 and is deposited in China General Microbiological Culture Collection Center addressed No. 3, Yard 1, Beichen West Road, Chaoyang District, Beijing on May 9, 2022, under the Budapest Treaty, with the preservation number of CGMCC NO. 40171, ensuring permanent availability and accessibility to the public upon grant of the patent. In order to better perform related research on the *Metarhizium rileyi*, the present invention further performs the deep research on the *Metarhizium rileyi* Mr006 to obtain a method for expanding propagation of the *Metarhizium rileyi* Mr006.

In the present invention, *Spodoptera frugiperda, Spodoptera litura, Pyrausta nubilalis, Helicoverpa armigera, Chilo suppressalis* and other test insects are selected as culture substrates, 2nd instar live insects are treated with a sub-lethal dose of chlorantraniliprole, the influences on the spore production time, spore yield and spore content of the *Metarhizium rileyi* Mr006 are analyzed, and a high-efficiency method for expanding propagation of *Metarhizium rileyi* Mr006 spores and a culture medium thereof are finally obtained by the analysis.

A first aspect of the present invention provides a method for expanding propagation of *Metarhizium rileyi* Mr006, comprising the following steps:

(1) culturing *Metarhizium rileyi* Mr006 spores to obtain a spore liquid; and (2) expanding propagation of the *Metarhizium rileyi* Mr006 spores: selecting noctuid insect larvae, treating same with a sub-lethal dose of chlorantraniliprole, spraying the spore liquid, concentrating the treated insect larvae into a sterile box, continuously feeding same with an artificial feed until death or pupation, observing the infection condition of the insect bodies, collecting spores after a 1st complete spore production, after the infected insects are subjected to moisture preservation, continuously performing culture and expanded propagation, and repeatedly collecting the spores for 1-2 times to obtain the maximum spore yield.

According to one embodiment of the present invention, step (1) culturing spores in the method for expanding propagation of *Metarhizium rileyi* Mr006 of the present invention comprises: preparing a culture medium for producing spores of the *Metarhizium rileyi* Mr006; sterilizing the culture medium and performing inoculation; and performing fermentation and culture to obtain a spore liquid.

According to one embodiment of the present invention, the noctuid insects in step (2) of the method for expanding propagation of *Metarhizium rileyi* Mr006 of the present invention are *Spodoptera frugiperda, Spodoptera litura* and *Helicoverpa armigera*, preferably, *Spodoptera litura*.

According to one embodiment of the present invention, the culture medium for producing spores of *Metarhizium rileyi* Mr006 of the present invention comprises 20-60 parts of rice, 10-20 parts of rice hulls, 2-4 parts of maltose, 8-16 parts of soybean powder, 2-8 parts of yeast powder, 30-60 parts of water, 1-2 parts of freeze-dried insect body powder, 0.1-0.2 part of zinc phosphate and 0.05-0.15 part of ferrous sulfate, wherein the freeze-dried insect body powder is freeze-dried *Spodoptera frugiperda* body powder.

According to one embodiment of the present invention, the culture medium for producing spores of *Metarhizium rileyi* Mr006 of the present invention comprises 40 parts of rice, 15 parts of rice hulls, 3 parts of maltose, 12 parts of soybean powder, 5 parts of yeast powder, 25 parts of water, 1.5 parts of freeze-dried *Spodoptera frugiperda* body powder, 0.15 part of zinc phosphate and 0.1 part of ferrous sulfate.

According to one embodiment of the present invention, the performing fermentation and culture to obtain a spore liquid of the present invention comprises performing culture in a 28° C. illumination incubator (16L/8D alternatively in the light and dark) for 3 d; adjusting the temperature to 24° C., continuously performing culture at the illumination (23L/1D alternatively in the light and dark) for 14 d, stopping fermentation to obtain conidium powder, washing down the conidia collected on a solid fermentation culture medium by using a polysorbate 80 (commercially known as Tween-80®) solution, and preparing same into a conidium liquid.

According to one embodiment of the present invention, the feeding condition in step (2) of the method for expanding propagation of *Metarhizium rileyi* Mr006 of the present invention is placing the insect bodies into an artificial climate box at the temperature of 27±1° C., the relative humidity of 70±5% and the photoperiod of 14L:10D for feeding.

According to one embodiment of the present invention, the present invention discloses a method for expanding propagation of *Metarhizium rileyi* Mr006, comprising (1) spraying *Metarhizium rileyi* Mr006 on 2nd instar live larvae of *Spodoptera litura* treated with a sub-lethal dose of chlorantraniliprole ($LC_{25}$ value of 0.008 μg/g) to cause infection; and (2) concentrating the 2nd instar larvae of the *Spodoptera litura* infected with the *Metarhizium rileyi* Mr006 into a sterile box, placing same into an artificial climate box at the temperature of 27±1° C., the relative humidity of 70±5% and the photoperiod of 14L:10D, continuously feeding same with an artificial feed until death or pupation, observing the infection condition of the insect bodies, collecting spores after a 1st complete spore production, after the infected insects are subjected to moisture preservation, continuously performing expanded propagation and culture, and repeatedly collecting the spores twice to obtain the maximum spore yield.

According to one embodiment of the present invention, the present invention discloses a control agent for noctuid insects at a pupal stage, containing a residual infected insect powder after expanding propagation of *Metarhizium rileyi* Mr006 spores, preferably, the infected insect powder is obtained by crushing the residual infected insect powder after expanding propagation of the *Metarhizium rileyi* Mr006 spores by using *Spodoptera litura* as a test insect. Preferably, a noctuid insect is *Spodoptera frugiperda*.

According to one embodiment of the present invention, the present invention discloses use of an infected insect powder prepared from residual infected insects after expanding propagation of *Metarhizium rileyi* Mr006 spores in a control agent for noctuid insects at a pupal stage.

Beneficial Effects

In the present invention, *Spodoptera frugiperda, Spodoptera litura, Pyrausta nubilalis, Helicoverpa armigera, Chilo suppressalis* and other test insects are selected as culture substrates for expanding propagation of *Metarhizium rileyi* Mr006, and the influences on the spore production time, spore yield and spore content are analyzed. It is found by tests that the *Spodoptera frugiperda, Spodoptera litura* and *Helicoverpa armigera* have significant effect on expanded propagation and spore production of the *Metarhizium rileyi* Mr006, particularly the average spore content of a live insect treatment of *Spodoptera litura* is the highest and reaches $13.5 \times 10^9$/g. The method of the present invention shortens the spore production time, increases the spore yield and content, updates the production processes, expands waste utilization, and reduces production costs. Therefore, the method is worthy of vigorously developing and promoting.

The *Metarhizium rileyi* Mr006 has been published in Chinese patent application No. CN202210572361.8 and is deposited in the China General Microbiological Culture Collection Center (CGMCC) at No. 3. Yard 1. Beichen West Road, Chaoyang District, Beijing, on May 9, 2022, under the preservation number CGMCC NO. 40171.

This deposit was made under the Budapest Treaty and meets the requirements of 37 C.F.R. 1.801-1.807. The deposited strain is permanently available and accessible to the public upon grant of a U.S. patent, with all restrictions on public access irrevocably removed upon patent issuance. The deposit will be maintained for at least 30 years from the date of deposit or for the enforceable life of the patent, whichever is longer, ensuring its viability and accessibility.

Further, during the pendency of this application, access to the deposit will be provided to persons entitled under 37 C.F.R. 1.14 and 35 U.S.C. § 122.

DETAILED DESCRIPTION

Materials and Treatment Methods of the Present Invention

*Metarhizium rileyi* Mr006: isolated from infected *Spodoptera frugiperda* by the laboratory and has been disclosed in Chinese patent application of No. CN202210572361.8. And the *Metarhizium rileyi* Mr006 is deposited in China General Microbiological Culture Collection Center addressed No. 3, Yard 1, Beichen West Road, Chaoyang District, Beijing on May 9, 2022, under the Budapest Treaty, with the preservation number of CGMCC NO. 40171, ensuring permanent availability and accessibility to the public upon grant of the patent.

Sabouraud maltose-yeast culture medium (SMAY culture medium): 4% of maltose, 1% of peptone, 1% of yeast extract powder and 1.5% of agar.

Freeze-dried *Spodoptera frugiperda* body powder: prepared from 6th instar larvae fed in the laboratory by ultralow-temperature freeze drying, and grinding and pulverizing under liquid nitrogen.

95.3% chlorantraniliprole raw pesticide: produced by FMC Agricultural Sciences Company (Shanghai).

Liquid seed culture medium: 4% of maltose, 1% of peptone, 1% of yeast extract powder, 0.15% of zinc sulfate and 0.1% of ferrous sulfate.

Solid fermentation culture medium: 20-60 parts of rice, 10-20 parts of rice hulls, 2-4 parts of maltose, 8-16 parts of soybean powder, 2-8 parts of yeast powder, 30-60 parts of water, 1-2 parts of freeze-dried insect body powder, 0.1-0.2 part of zinc phosphate and 0.05-0.15 part of ferrous sulfate, wherein the freeze-dried insect body powder is freeze-dried *Spodoptera frugiperda* body powder.

Feed for insects: prepared according to the requirements of conventional feeding conditions of 5 test insects of *Spodoptera frugiperda, Spodoptera litura, Pyrausta nubilalis, Helicoverpa armigera* and *Chilo suppressalis*.

Start time for spore production: in the process of infection of larvae, when the infected insect bodies begins to generate green powder, the powder is immediately picked out and checked under a microscope, and after the powder is determined to be conidium spores, the start time for spore production is determined.

Spore counting: the collected spore powder after culture is finished is scraped from the insect bodies or collected by using a spore collector, directly weighed, and then put into a 100-ml conical flask. Sterile water containing 0.05% of polysorbate 80 is added, the mixture is stirred on a magnetic stirrer for 30 min to sufficiently disperse the spores so as to prepare a uniform spore suspension, and the spore amount is determined by using a hemocytometer.

Example 1 Screening of Dominant Test Insects

Larvae were respectively fed to about 2nd instar according to feeding conditions of 5 test insects of *Spodoptera* frugiperda, Spodoptera litura, Pyrausta nubilalis, Helicoverpa armigera and Chilo suppressalis for an infection test. The larvae were cultured with an SMAY culture medium to obtain a spore powder of Metarhizium rileyi Mr006, the concentration of a spore suspension was set to be 1×10$^7$/mL, the consistently growing 2nd instar Spodoptera frugiperda, Spodoptera litura, Pyrausta nubilalis, Helicoverpa armigera and Chilo suppressalis larvae were selected for 5 treatments with 20 insects each time for 4 repeated times. The larvae were soaked with the spore suspension. An infection standard was that the larvae stopped eating, the insect bodies were infected or the surfaces of the larvae produced spores, and the infection rate of the larvae after 10 days was detected.

According to screening, it was found by referring to table 1 that the Metarhizium rileyi Mr006 had the infection activity on the 5 2nd instar test insects of the Spodoptera frugiperda, Spodoptera litura, Pyrausta nubilalis, Helicoverpa armigera and Chilo suppressalis. When the concentration was 1×10$^7$ spores/ml, the infection rate after 10 days was 71.25%, 81.25%, 38.75%, 68.75% and 36.25% respectively; the infection rate of the Spodoptera frugiperda, Spodoptera litura and Helicoverpa armigera was higher than that of the Pyrausta nubilalis and Chilo suppressalis. Therefore, compared with the pyralid pests, the infection rate of the Metarhizium rileyi Mr006 to the noctuid insects was higher. Therefore, the infection of the noctuid insects facilitated the propagation of the spores in the insect bodies.

TABLE 1

Infection rate of Metarhizium rileyi Mr006 on 5 larvae

| Concentration of Metarhizium rileyi Mr006 spores (spores/mL) | Name of test insects | Number of test insects | Number of infected insects | Infection rate (%) |
| --- | --- | --- | --- | --- |
| 1 × 10$^7$ | Spodoptera frugiperda | 80 | 57 | 71.25 |
|  | Spodoptera litura | 80 | 65 | 81.25 |
|  | Pyrausta nubilalis | 80 | 31 | 38.75 |
|  | Helicoverpa armigera | 80 | 55 | 68.75 |
|  | Chilo suppressalis | 80 | 29 | 36.25 |

In addition, according to the growth characteristics of the insect bodies, the noctuid Spodoptera frugiperda, Spodoptera litura and Helicoverpa armigera bodies in the same instar were larger than the pyralid Pyrausta nubilalis and Chilo suppressalis. Therefore, the single noctuid insect body had higher potential for obtaining the spores. Therefore, the Spodoptera frugiperda, Spodoptera litura and Helicoverpa armigera were selected as dominant test insects in a subsequent test for expanding propagation of spores.

Example 2 Culture and Expanded Propagation of Metarhizium rileyi Mr006 Spores 40 parts of rice, 15 parts of rice hulls, 0.3 part of maltose, 15 parts of soybean powder, 5 parts of yeast powder, 1.5 parts of freeze-dried Spodoptera frugiperda body powder, 0.15 part of zinc phosphate, 0.1 part of ferrous sulfate and 23.5 parts of water were selected to be prepared into culture raw materials; the evenly mixed raw materials were stood and soaked for 4 h, bagged, and autoclaved-sterilized at 121° C. for 50 min, after the temperature was reduced to 30° C., a Metarhizium rileyi Mr006 liquid seed liquid was inoculated at the inoculation amount of 10% and evenly stirred and mixed, and the strain was firstly cultured in a 28° C. illumination incubator (16L/8D alternatively in the light and dark) for 3 d, the temperature was adjusted to 24° C., the strain was continuously cultured at the illumination (23L/1D alternatively in the light and dark) for 14 d, and fermentation was stopped to obtain conidium powder. The conidia collected on a solid fermentation culture medium was washed down by using a polysorbate-80 solution and prepared into a conidium liquid at 10$^7$ spores/mL for later use.

Dead insect treatment: each 80 of 3 2nd instar test insects of Spodoptera frugiperda, Spodoptera litura and Helicoverpa armigera were selected, autoclaved-sterilized at 121° C. for 15 min to obtain dead insects, the prepared Metarhizium rileyi Mr006 conidium liquid at 10$^7$ spores/mL was respectively sprayed, and then the infected insects were concentrated into a sterile box and placed into an artificial climate box at the temperature of (27±1° C.), the relative humidity of (70±5) % and the photoperiod of 14L:10D. The infection condition of the insect bodies was observed respectively, spores were collected after a 1st complete spore production, after the infected insects were subjected to moisture preservation, culture was continuously performed, and the spores were repeatedly collected twice to obtain the maximum spore yield.

Live insect treatment: each 80 of 3 2nd instar test insects of Spodoptera frugiperda, Spodoptera litura and Helicoverpa armigera were selected, the prepared Metarhizium rileyi Mr006 conidium liquid at 10$^7$ spores/mL was respectively sprayed, and then the infected insects were concentrated into a sterile box, placed into an artificial climate box at the temperature of (27±1° C.), the relative humidity of (70±5) % and the photoperiod of 14L:10D, and continuously fed with an artificial feed until death or pupation. The infection condition of the insect bodies was observed respectively, spores were collected after a 1st complete spore production, after the infected insects were subjected to moisture preservation, culture was continuously performed, and the spores were repeatedly collected twice to obtain the maximum spore yield.

Live insect pesticide treatment: each 80 of 3 2nd instar test insects of Spodoptera frugiperda, Spodoptera litura and Helicoverpa armigera were selected and respectively treated with a sub-lethal dose of chlorantraniliprole (LC$_{25}$ values were 0.006, 0.008 and 0.015 µg/g successively), the prepared Metarhizium rileyi Mr006 conidium liquid at 10$^7$ spores/mL was respectively sprayed, and then the infected insects were concentrated into a sterile box, placed into an artificial climate box at the temperature of (27±1° C.), the relative humidity of (70±5) % and the photoperiod of 14L:10D, and continuously fed with an artificial feed until death or pupation. The infection condition of the insect bodies was observed respectively, spores were collected after a 1st complete spore production, after the infected insects were subjected to moisture preservation, culture was continuously performed, and the spores were repeatedly collected twice to obtain the maximum spore yield.

The results showed that all 3 2nd instar test insects of the Spodoptera frugiperda, Spodoptera litura and Helicoverpa armigera can be used for expanding propagation of Metarhizium rileyi Mr006 spores, but the spore production time, spore yield and spore content were different among the different treatments. After the larvae were treated with the sub-lethal dose of chlorantraniliprole, the metabolism was down-regulated and the activity was slowed down, thereby facilitating the infection. The results were shown in table 2 that the spore production time was shortened to 4-7 days, which was the shortest (4-5 days) for the *Spodoptera litura* after the treatments, 5-6 days for the *Spodoptera frugiperda* and 5-7 days for the *Helicoverpa armigera*. Spores of 3 test insects of the *Spodoptera frugiperda*, *Spodoptera litura* and *Helicoverpa armigera* can all be collected for 3 times, and the average spore yield of the live insect treatment was higher than that of the dead insect treatment; the 1st time spore collection amount was the highest, the spore collection amount in the two subsequent treatments began to reduce, and the reduction range of the dead insect treatment was higher than that of the live insect treatment; and the total average spore yield of 3 times was the highest and reached 1.76 g/insect of the live insect pesticide treatment of the *Spodoptera litura* and was 1.69 g/insect of the live insect treatment of the *Spodoptera litura*, and the total average spore yield of 3 times of the same test insect was higher in the live insect pesticide treatment than the live insect treatment and the dead insect treatment. The average spore content of 3 test insects of the *Spodoptera frugiperda*, *Spodoptera litura* and *Helicoverpa armigera* was higher in the live insect pesticide treatment than the live insect treatment and the dead insect treatment. The average spore content was the highest and reached $14.3 \times 10^9$/g of the live insect pesticide treatment of the *Spodoptera litura*, $13.5 \times 10^9$/g of the live insect treatment of the *Spodoptera litura*, and $12.6 \times 10^9$/g of the live insect pesticide treatment of the *Spodoptera frugiperda*. In the 3 test insects, the spore production time, total average spore yield of 3 times and the average spore content after the live insect pesticide treatment for expanding propagation of *Spodoptera litura* spores were all superior to those of the *Spodoptera frugiperda* and *Helicoverpa armigera*. After the spores were collected, the infected insects can still produce spores after being subjected to moisture preservation, and the insect bodies can also be used as organic matters and can be processed into a microbial fertilizer after being crushed for pest control and crop growth.

According to the method record in Chinese patent application of No. CN202210572361.8 for culturing spores by using a culture substrate, various substrate raw materials were required to be selected, weighed proportionally and sterilized, the raw materials cannot be reused and the spores can only be collected at one time. Nevertheless, using the *Spodoptera litura* and other test insects for expanding propagation of the *Metarhizium rileyi* Mr006 spores only requires to feed the larvae, and the strain can be cultured for multiple times for collecting the spores. Besides, after the 2nd instar larvae were treated with the sub-lethal dose of chlorantraniliprole ($LC_{25}$ value was 0.008 μg/g), indexes such as the spore production time, total average spore yield of 3 times and average spore content were superior to those of the single live insect and dead insect treatments. In addition, most spores obtained by using the culture substrate were mixed with the substrate, and therefore, the separation difficulty was higher and the collection efficiency was low. However, the spores obtained by expanding propagation of the insect bodies had higher purity, were easy to separate from the insect bodies, and can be directly collected only by manual shaking or a spore collector. Therefore, compared with using the culture substrate to culture the spores, using the *Spodoptera litura* as a test insect for expanding propagation of the *Metarhizium rileyi* Mr006 spores was relatively simple in process and easy to operate.

Example 3: Control of *Spodoptera frugiperda* by Using *Metarhizium rileyi* Mr006

36 pots of sterile soil were selected indoors, 20 mature *Spodoptera frugiperda* larvae were respectively inoculated, namely each treatment was performed in 4 pots, a total of 80 pupae. After the spored were collected, infected *Spodoptera litura*, *Spodoptera frugiperda* and *Helicoverpa armigera* larvae (live insect treatment and dead insect treatment) were crushed to obtain an infected insect powder, 10 g of the infected insect powder was sprayed into each pot, was

TABLE 2

Test results of expanded propagation of *Metarhizium rileyi* Mr006 bodies

| Name of test insects | Treatment method | Spore production time (D) | 1st average spore yield (g/insect) | 2nd average spore yield (g/insect) | 3rd average spore yield (g/insect) | Total average spore yield of 3 times (g/insect) | Average spore content ($10^9$/g) |
|---|---|---|---|---|---|---|---|
| *Spodoptera frugiperda* | Live insect pesticide treatment | 5 | 0.87 | 0.46 | 0.13 | 1.46 | 12.6 |
| | Live insect treatment | 6 | 0.86 | 0.43 | 0.15 | 1.44 | 12.1 |
| | Dead insect treatment | 5 | 0.83 | 0.23 | 0.08 | 1.14 | 11.8 |
| *Spodoptera litura* | Live insect pesticide treatment | 4 | 0.99 | 0.51 | 0.26 | 1.76 | 14.3 |
| | Live insect treatment | 5 | 0.96 | 0.52 | 0.21 | 1.69 | 13.5 |
| | Dead insect treatment | 4 | 0.91 | 0.31 | 0.15 | 1.37 | 12.3 |
| *Helicoverpa armigera* | Live insect pesticide treatment | 5 | 0.86 | 0.3 | 0.12 | 1.28 | 12.1 |
| | Live insect treatment | 7 | 0.85 | 0.32 | 0.18 | 1.35 | 11.8 |
| | Dead insect treatment | 5 | 0.82 | 0.18 | 0.05 | 1.05 | 11.5 | placed into a greenhouse to be subjected to moisture preservation, and subjected to isolated culture for 10 days. The infection rate of the *Spodoptera frugiperda* pupae per pot was examined.

The results were shown in table 3, the infected *Spodoptera frugiperda*, *Spodoptera litura* and *Helicoverpa armigera* powders infected with the *Metarhizium rileyi* Mr006 all had good infectivity on the *Spodoptera frugiperda* pupae. After the administration for 10 days, the infection rate of the 3 treatments was 46.25%, 41.25% and 48.75% respectively of the *Spodoptera litura* test insect, was 37.25%, 32.50% and 41.25% respectively of the *Spodoptera frugiperda* test insect, and was 28.75%, 26.25% and 31.25% respectively of the *Helicoverpa armigera* test insect. The infectivity of the infected insect powder after the live insect pesticide treatment of the same test insect was higher that after the single live insect and dead insect treatments, wherein the infectivity was the highest after the pesticide treatment of the *Spodoptera litura*. After the *Spodoptera litura* treated by a sub-lethal dose of chlorantraniliprole ($LC_{25}$ value was 0.008 μg/g) was used as a test insect to expand propagation of the *Metarhizium rileyi* Mr006 spores, the residual infected insect powder had a better infection effect on the *Spodoptera frugiperda* pupae and therefore, can be used for controlling the *Spodoptera frugiperda* at a pupal stage.

TABLE 3

Use effect of *Metarhizium rileyi* Mr006 in control of *Spodoptera frugiperda*

| Treatment | | Dose and administration method | Number of test insects | Number of infected insects | Infection rate after 10 days of administration (%) |
|---|---|---|---|---|---|
| *Spodoptera frugiperda* | Live insect | 10 grams of infected insects are applied per pot | 80 | 30 | 37.5 |
| | Dead insect | | 80 | 26 | 32.5 |
| | Live insect pesticide | | 80 | 33 | 41.25 |
| *Spodoptera litura* | Live insect | | 80 | 37 | 46.25 |
| | Dead insect | | 80 | 33 | 41.25 |
| | Live insect pesticide | | 80 | 39 | 48.75 |
| *Helicoverpa armigera* | Live insect | | 80 | 23 | 28.75 |
| | Dead insect | | 80 | 21 | 26.25 |
| | Live insect pesticide | | 80 | 25 | 31.25 |

The present invention is further described in detail in combination of the above content and the specific embodiments, but it cannot be considered that the specific embodiments of the present invention only limit these descriptions. Numerous simple deductions or substitutions can further be made by those of ordinary skill in the art to which the present invention pertains without departing from the concepts of the present invention, which shall be deemed to fall within the protection scope defined by the appended claims of the present invention.

What is claimed is:

1. A method for expanding propagation of *Metarhizium rileyi* Mr006, comprising the following steps:

(1) culturing *Metarhizium rileyi* Mr006 spores to obtain a spore liquid; and (2) expanding propagation of the *Metarhizium rileyi* Mr006 spores by: selecting noctuid insect larvae from *Spodoptera frugiperda*, *Spodoptera litura* and *Helicoverpa armigera*, treating same with a sub-lethal dose of chlorantraniliprole, spraying the spore liquid onto the noctuid insect larvae, concentrating the treated insect larvae into a sterile box, continuously feeding same with an artificial feed until death or pupation, observing the infection condition of the insect bodies, collecting spores after a 1 st complete spore production, after the infected insects are subjected to moisture preservation, continuously performing culture and expanded propagation, and repeatedly collecting the spores for 1-2 times to obtain the maximum spore yield;

the *Metarhizium rileyi* Mr006 is deposited in China General Microbiological Culture Collection Center addressed No. 3, Yard 1, Beichen West Road, Chaoyang District, Beijing on May 9, 2022, under the Budapest Treaty, with the preservation number of CGMCC NO. 40171, ensuring permanent availability and accessibility to the public upon grant of the patent.

2. The method according to claim 1, wherein step (1) culturing spores in the method for expanding propagation of *Metarhizium rileyi* Mr006 comprises: preparing a culture medium for producing spores of the *Metarhizium rileyi* Mr006; sterilizing the culture medium and performing inoculation; and performing fermentation and culture to obtain a spore liquid.

3. The method according to claim 2, wherein the culture medium comprises 20-60 parts of rice, 10-20 parts of rice hulls, 2-4 parts of maltose, 8-16 parts of soybean powder, 2-8 parts of yeast powder, 30-60 parts of water, 1-2 parts of freeze-dried insect body powder, 0.1-0.2 part of zinc phosphate and 0.05-0.15 part of ferrous sulfate, wherein the freeze-dried insect body powder is freeze-dried *Spodoptera frugiperda* body powder.

4. The method according to claim 3, wherein the culture medium comprises 40 parts of rice, 15 parts of rice hulls, 3 parts of maltose, 12 parts of soybean powder, 5 parts of yeast powder, 25 parts of water, 1.5 parts of freeze-dried *Spodoptera frugiperda* body powder, 0.15 part of zinc phosphate and 0.1 part of ferrous sulfate.

5. The method according to claim 2, wherein the performing fermentation and culture to obtain a spore liquid comprises performing culture in a 28° C. illumination incubator at the illumination condition of 16L/8D alternatively in the light and dark for 3 d; adjusting the temperature to 24° C., continuously performing culture at the illumination condition of 23L/1D alternatively in the light and dark for 14 d, stopping fermentation to obtain conidium powder, washing down the conidia collected on a solid fermentation culture medium by using a polysorbate 80 solution, and preparing same into a conidium liquid.

6. The method according to claim 1, wherein the feeding condition in step (2) of the method for expanding propagation of *Metarhizium rileyi* Mr006 is placing the insect bodies into an artificial climate box at the temperature of 27±1° C., the relative humidity of 70±5% and the photoperiod of 14L:10D for feeding.

7. A method for expanding propagation of *Metarhizium rileyi* Mr006, comprising the following steps: (1) spraying *Metarhizium rileyi* Mr006 on 2nd instar live larvae of *Spodoptera litura* treated with a sub-lethal dose of chlorantraniliprole to cause infection, the sub-lethal dose is a $LC_{25}$ value of 0.008 μg/g; and (2) concentrating the 2nd instar larvae of the *Spodoptera litura* infected with the *Metarhizium rileyi* Mr006 into a sterile box, placing same into an artificial climate box at the temperature of 27±1° C., the relative humidity of 70±5% and the photoperiod of 14L:10D, continuously feeding same with an artificial feed until death or pupation, observing the infection condition of the insect bodies, collecting spores after a 1st complete spore production, after the infected insects are subjected to moisture preservation, continuously performing expanded propagation and culture, and repeatedly collecting the spores twice to obtain the maximum spore yield;

the *Metarhizium rileyi* Mr006 is deposited in China General Microbiological Culture Collection Center addressed No. 3, Yard 1, Beichen West Road, Chaoyang District, Beijing on May 9, 2022, under the Budapest Treaty, with the preservation number of CGMCC NO. 40171 ensuring permanent availability and accessibility to the public upon grant of the patent.

* * * * *